(12) United States Patent
Merkle

(10) Patent No.: US 7,244,236 B2
(45) Date of Patent: Jul. 17, 2007

(54) SPECIMEN TRAP WITH STRAINER

(75) Inventor: William L. Merkle, Elizabeth, IL (US)

(73) Assignee: M D Technologies inc., Elizabeth, IL (US)

( * ) Notice: Subject to any disclaimer, the term of this patent is extended or adjusted under 35 U.S.C. 154(b) by 210 days.

(21) Appl. No.: 10/847,191

(22) Filed: May 17, 2004

(65) Prior Publication Data
US 2004/0230135 A1    Nov. 18, 2004

Related U.S. Application Data

(60) Provisional application No. 60/471,497, filed on May 16, 2003.

(51) Int. Cl.
*A61B 5/00* (2006.01)

(52) U.S. Cl. ............... 600/575; 600/573; 600/576; 600/577; 600/578; 600/579; 600/580; 604/319

(58) Field of Classification Search .......... 604/319, 604/4.01, 5.01, 6.09; 600/575, 573, 580
See application file for complete search history.

(56) References Cited

U.S. PATENT DOCUMENTS

| | | | | |
|---|---|---|---|---|
| 2,115,577 A | * | 4/1938 | Goldman | 210/494.1 |
| 3,194,069 A | * | 7/1965 | Scott | 73/219 |
| 3,699,815 A | * | 10/1972 | Holbrook | 73/427 |
| 3,855,997 A | | 12/1974 | Sauer | |
| 3,965,902 A | | 6/1976 | Reilly et al. | |
| 4,018,061 A | * | 4/1977 | Williamitis | 62/125 |
| 4,045,346 A | * | 8/1977 | Swaskey | 210/164 |
| 4,228,798 A | * | 10/1980 | Deaton | 604/540 |
| 4,312,351 A | | 1/1982 | Kurtz et al. | |
| 4,353,868 A | * | 10/1982 | Joslin et al. | 422/101 |
| 4,384,580 A | | 5/1983 | Leviton | |
| 4,388,922 A | | 6/1983 | Telang | |
| 4,643,197 A | * | 2/1987 | Greene et al. | 600/575 |
| 4,656,997 A | * | 4/1987 | Morales-George | 128/897 |
| 4,704,106 A | | 11/1987 | Shave et al. | |
| 4,729,764 A | * | 3/1988 | Gualtier | 604/38 |
| 4,761,227 A | * | 8/1988 | Willinger et al. | 210/169 |
| 4,852,560 A | * | 8/1989 | Hermann et al. | 600/575 |
| 5,105,824 A | * | 4/1992 | Rasch | 600/575 |
| 5,133,374 A | | 7/1992 | Druding et al. | |
| 5,286,262 A | | 2/1994 | Herweck et al. | |
| 5,423,792 A | * | 6/1995 | Oxley | 604/409 |
| 5,575,293 A | | 11/1996 | Miller et al. | |
| 5,624,418 A | * | 4/1997 | Shepard | 604/319 |
| 5,720,299 A | | 2/1998 | Theodoru | |
| 5,792,126 A | | 8/1998 | Tribastone et al. | |

(Continued)

*Primary Examiner*—Max Hindenburg
*Assistant Examiner*—Kristin D. Rogers
(74) *Attorney, Agent, or Firm*—Pauley Petersen & Erickson

(57) ABSTRACT

A specimen trap including a container forming a chamber. A strainer is fixedly positioned within the chamber and defines an upper portion of the chamber and a lower portion of the chamber. The strainer has a porous surface that provides fluidic communication between the upper portion and the lower portion. One tube connection is mounted to the cap and forms a passage through the cap and another tube extends through the cap and through the strainer into the lower portion. The cap is rotatable with respect to the container to form communication between one of the specimen compartments and the one tube connection passage for collection of an independent specimen.

27 Claims, 3 Drawing Sheets

U.S. PATENT DOCUMENTS

| | | | |
|---|---|---|---|
| 5,897,840 A * | 4/1999 | Owens et al. | 422/102 |
| 6,149,634 A * | 11/2000 | Bernabei | 604/319 |
| 6,152,902 A | 11/2000 | Christian et al. | |
| 6,589,219 B1 * | 7/2003 | Shibuya | 604/319 |
| 6,626,877 B2 * | 9/2003 | Anderson et al. | 604/319 |
| 2001/0037096 A1 * | 11/2001 | Anderson et al. | 604/322 |
| 2004/0102743 A1 * | 5/2004 | Walker | 604/319 |
| 2005/0065454 A1 * | 3/2005 | Manoussakis | 600/576 |

* cited by examiner

SPECIMEN TRAP WITH STRAINER

CROSS REFERENCE TO RELATED APPLICATIONS

This application claims the benefit of U.S. Provisional Application No. 60/471,497, filed 16 May 2003.

BACKGROUND OF THE INVENTION

1. Field of the Invention

This invention relates to a specimen trap having a strainer for collecting fluid-borne specimens.

2. Discussion of Related Art

In medical procedures where body fluid is removed using suction, it is often desirable to isolate solid particles for pathological analysis. A common method for isolating solid particles from suctioned fluid is to collect a sample of the fluid containing the desired solid specimen, and strain the fluid sample using a straining medium (gauze, urine strainer, etc.). Design of existing specimen collectors results in the solid specimen entering a container that contains fluid. Since the container is connected to a suction source, it is common for the solid specimen to travel across the surface of the fluid within the container and be removed from the container by suction. In the health care profession, numerous devices are available for collecting fluid samples; however, these are not well-suited for retrieving solid particles from fluid because the devices lack either a straining device, or a tube to remove strained fluid from the container, or both.

There is an apparent need for a specimen retrieval device to be used in medical procedures where isolation of solid particles (e.g. tissue) collected with suctioned fluids is desirable.

SUMMARY OF THE INVENTION

It is one object of this invention to provide an improved specimen trap for separating fluid-borne solid particles and materials from suctioned fluids.

It is another object of this invention to provide a specimen trap for retrieving or collecting multiple independent specimens.

The above and other objects of the invention can be attained through a specimen trap including a container forming a chamber. A strainer is fixedly positioned within the chamber and defines an upper portion of the chamber and a lower portion of the chamber. The strainer has a porous surface that provides fluidic communication between the upper portion and the lower portion. In one preferred embodiment of this invention, a plurality of supports are connected to the strainer. Each support extends to a bottom surface of the container to maintain the strainer in a fixed position within the chamber.

A cap is mounted with respect to the container. The cap can be threadedly connected to the container or the cap can be press-fitted onto the container and rotatable with respect to the container. A first tube connection, such as a field tube connection, is mounted to the cap and forms a passage through the cap and in communication with the upper portion. A second tube, such as a transfer tube, extends through the cap and through the strainer into the lower portion, and forms a passage in communication with the lower portion. The transfer tube preferably forms a shoulder that interferes with the strainer to maintain the strainer in the fixed position within the chamber.

In one preferred embodiment of this invention, the specimen trap includes a dividing element that extends from a top surface of the strainer and forms a plurality of specimen compartments. Preferably, the dividing element includes a plurality of dividers that extend from a top surface of the strainer to form the specimen compartments. Each divider preferably extends radially outwardly from a center point of the strainer, and upwardly between the top surface of the strainer and the cap. The cap is rotatable with respect to the container to form communication between one of the specimen compartments and the field tube connection passage for collection of an independent specimen.

Other objects and advantages of the invention are apparent to those skilled in the art, in view of the following detailed description taken in conjunction with the appended claims and drawings.

DETAILED DESCRIPTION OF THE INVENTION

Figure 1:
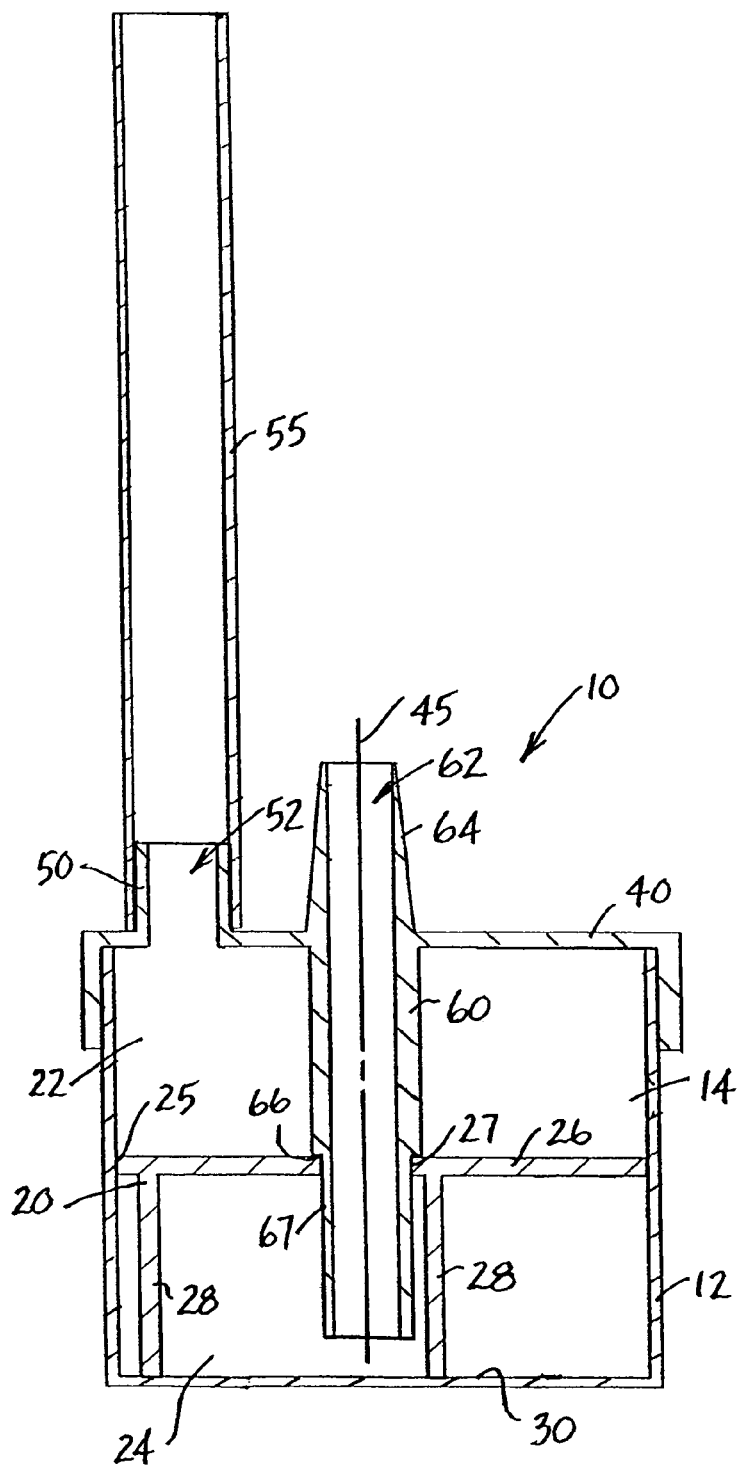
FIG. 1 is a sectional side view of a specimen trap, according to one preferred embodiment of this invention.

The present invention provides a specimen trap 10 for collecting or capturing fluid-borne specimens in procedures where suction is used to collect fluids. Specimen trap 10 includes a container 12 that forms or defines a chamber 14. A strainer 20 is positioned within chamber 14 to define an upper portion of the chamber 22 and a lower portion of the chamber 24. In one preferred embodiment of this invention, a volume of upper portion 22 is about equal to a volume of lower portion 24. Alternatively, the upper portion volume may be different than the lower portion volume. For example, in one preferred embodiment of this invention, the upper portion volume is greater than the lower portion volume.

Figures 2, 3:
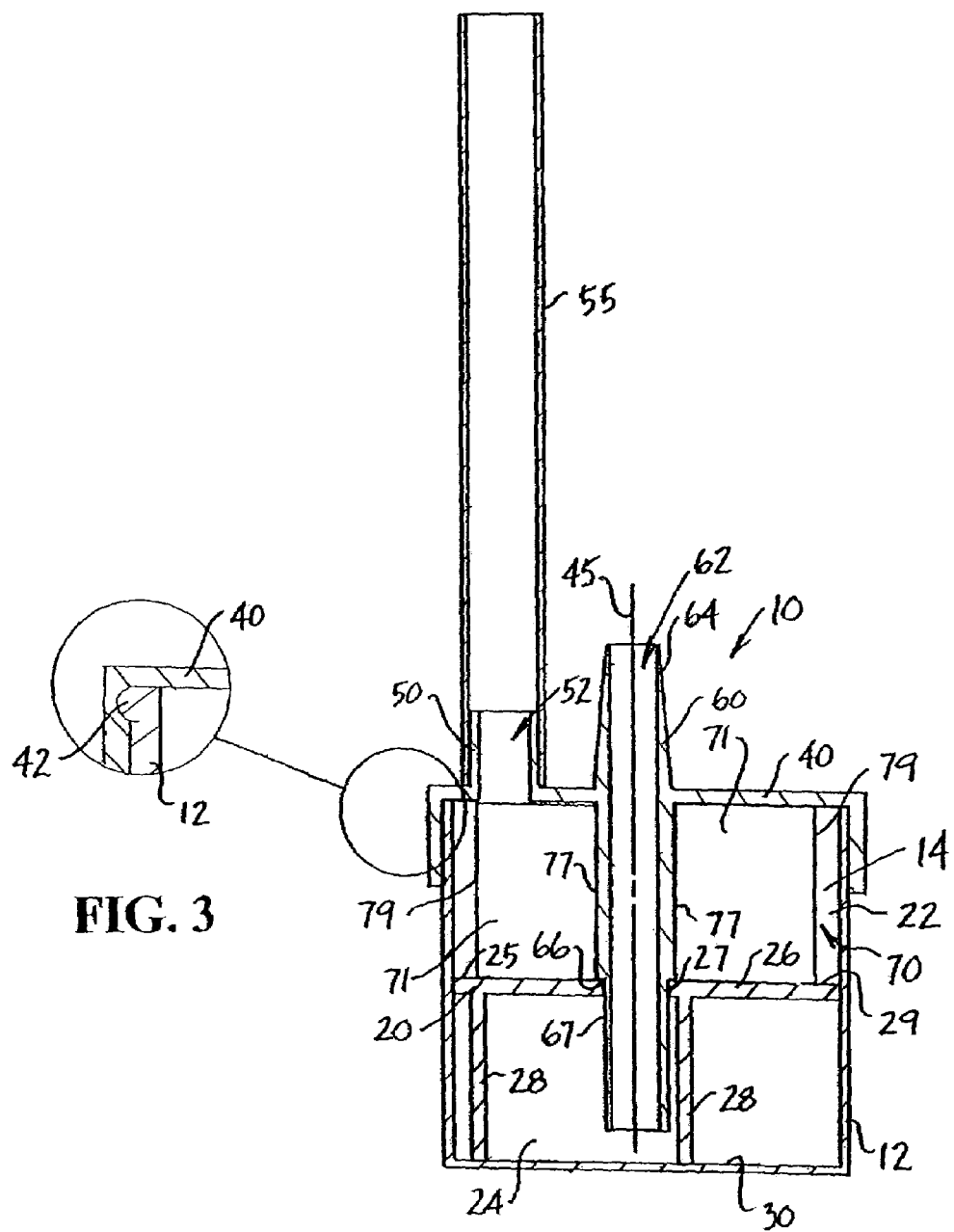
FIG. 2 is a sectional side view of a specimen trap, according to one preferred embodiment of this invention.
FIG. 3 is an enlarged view of a portion of the specimen trap of FIG. 2 showing a cap rotatably mounted to a container, according to one preferred embodiment of this invention.

Preferably, strainer 20 is fixedly or securely positioned within chamber 14 and extends to or terminates at an inner wall surface 25 of container 12 to prevent specimen material, including body fluids and solid particles, such as tissue, from moving or flowing between upper portion 22 and lower portion 24 between a periphery of strainer 20 and inner wall surface 25. As shown in FIGS. 1 and 2, for example, a periphery of strainer 20 contacts inner wall surface 25.

Figure 4:
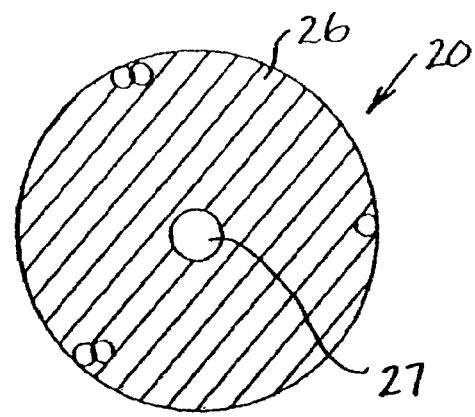
FIG. 4 is a top view of a specimen trap strainer, according to one preferred embodiment of this invention.
Figure 5:
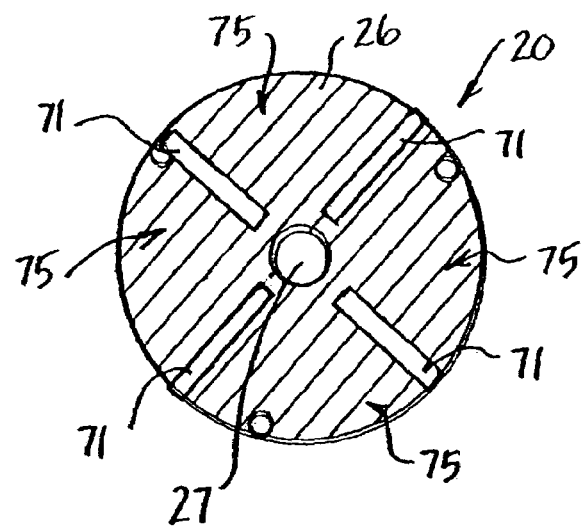
FIG. 5 is a top view of a specimen trap strainer, according to one preferred embodiment of this invention.

Strainer 20 includes a porous surface 26 that provides fluidic communication between upper portion 22 and lower portion 24. Preferably, porous surface 26 extends across a cross-sectional area of chamber 14 and terminates at the strainer periphery, abutting against or contacting inner wall surface 25. Porous surface 26 may be made of any suitable porous surface and/or material that allows or permits fluids to flow through strainer 20 but prevents solid particles or materials from flowing or moving through strainer 20. For example, porous surface 26 can be made of a suitable plastic material forming a plurality of apertures or holes that allow fluid flow but have dimensions small enough to prevent solid particles or materials from moving through the apertures or holes. Alternatively, porous surface 26 can be made of a suitable plastic, metal, composite or fabric material, including any suitable screen or mesh material. It is apparent to those skilled in the art and guided by the teachings herein provided that other materials may be suitable for forming or making porous surface 26. Referring to FIGS. 4 and 5, strainer 20 forms or includes a void 27 through porous surface 26. Void 27 is preferably positioned generally about a center point of strainer 20 and porous surface 26.

In one preferred embodiment of this invention, at least one and preferably a plurality of supports 28 are connected to strainer 20. Each support 28 extends from strainer 20 to a bottom surface 30 of container 12. Preferably, but not necessarily, each support 28 is positioned at a periphery of strainer 20 and against inner wall surface 25. Each support 28 contacts bottom surface 30 to maintain strainer 20 in a fixed or secured position within chamber 14. Preferably, supports 28 are molded or integrated with strainer 20. For example, strainer 20 and supports 28 can be molded of a suitable plastic material using molding techniques and methods known to those having ordinary skill in the art and guided by the teachings herein provided. Alternatively, each support 28 may comprise an independent or separate material piece that is connected or attached to strainer 20.

A cap 40 is mounted or connected with respect to container 12 and covers an opening of chamber 14. In one preferred embodiment of this invention, cap 40 is press-fitted onto container 12, as shown in FIGS. 1–3, to create a substantially airtight seal. Referring further to FIG. 3, in one preferred embodiment of this invention, container 12 forms a bead or lip 42 about a periphery of the chamber opening, which forms a substantially airtight seal about the chamber opening while allowing cap 40 to rotate with respect to or relative to container 12 about a rotational axis 45 of cap 40, as discussed in further detail below. Alternatively, cap 40 can be threadedly connected to container 12, as is known to those having ordinary skill in the art.

As shown in FIGS. 1 and 2, a first tube connection, such as a field tube connection 50, is mounted or connected to cap 40. Field tube connection 50 forms a passage 52 through cap 40 and in communication with upper portion 22. Preferably, field tube connection 50 is positioned at a periphery of cap 40 to allow cap 40 to rotate with respect to container 12. Passage 52 provides communication between a suction field (not shown) and upper portion 22. A connecting tube 55 can be connected to field tube connection 50. The connecting tube is preferably connected to additional tubing, a catheter, an endoscope or any suitable device that directly contacts the suction field. Body fluids and solid particles, such as body tissue, removed from the suction field are transferred from the suction field through connecting tube 55 and passage 52 into upper portion 22. The body fluids continue to move or flow through porous surface 26 into lower portion 24 while the solid particles remain contained within upper portion 22.

A second tube, such as a transfer tube 60, extends through cap 40 and through strainer 20 at void 27 into lower portion 24. Preferably, transfer tube 60 is coaxially positioned along cap rotational axis 45 to allow cap 40 to rotate with respect to container 12. Transfer tube 60 forms a passage 62 in communication with lower portion 24, which provides communication between lower portion 24 and a suction source (not shown) through a suction tube connectable or mountable to a free end portion 64 of transfer tube 60. As shown in FIGS. 1 and 2, transfer tube 60 extends into lower portion 24 and terminates preferably short of bottom surface 30. In one preferred embodiment of this invention, transfer tube 60 forms a shoulder 66, which contacts and/or interferes with strainer 20 to maintain strainer 20 in the fixed or secured position within chamber 14. Thus, supports 28 and/or shoulder 66 prevents strainer 20 from falling to a lower level within chamber 14 and/or raising to a higher level within chamber 14.

Upon activation of the suction source or a vacuum, bodily fluids are removed from lower portion 24 through transfer tube passage 62, which preferably results in a suction or vacuum condition within chamber 14 as well as within connecting tube 55. The suction or vacuum draws specimen matter, including body fluids and solid particles, from the suction field into connecting tube 55. The specimen matter passes through passage 52 and into upper portion 22, and is directed towards porous surface 26. The solid particles are trapped by porous surface 26 and contained within upper portion 22. The strained body fluids pass or flow through porous surface 26 into lower portion 24. Body fluids collected in lower portion 24 pass or flow through transfer tube 62 and exit container 12 through the suction tube connected at transfer tube free end portion 64. Free end portion 64 can have a tapered external shape, such as shown in FIGS. 1 and 2, or can have any other suitable external shape that accommodates each of differently sized discharge tubes, for example that have different inner diameters.

In one preferred embodiment of this invention, specimen trap 10 includes a dividing element 70 extending from top surface 29 of strainer 20 and forming a plurality of specimen compartments 75. Preferably, but not necessarily, dividing element 70 is integrated with strainer 20. Alternatively, dividing element 70 can be an independent material piece that is fitted or connected to strainer 20. Dividing element 70 includes at least one divider 71 extending from top surface 29. Preferably, a plurality of dividers 71, for example four dividers 71 as shown in FIG. 5, extend from top surface 29. In one preferred embodiment of this invention, each divider 71 extends radially outwardly from a center point of strainer 20. Referring to FIGS. 1 and 2, the strainer center point is preferably aligned with cap rotational axis 45. Further, each divider 71 preferably extends upwardly between top surface 29 of strainer 20 and cap 40. Dividers 71 form specimen compartments 75. For example, adjacent dividers 71 form one specimen compartment 75 between the adjacent dividers. In this embodiment, multiple independent specimens can be retrieved and/or collected by rotating cap 40 with respect to container 12 through any suitable angle. Preferably, but not necessarily, dividers 71 are equally spaced about top surface 29 so that cap 40 can be rotated through a suitable angle generally equal to 360° divided by the number of dividers 71 to form communication between one selected or desired specimen compartment 75 and field tube passage 52.

Referring to FIG. 2, with transfer tube 60 positioned through void 27 formed by strainer 20, transfer tube shoulder 66 contacts and/or interferes with strainer top surface 29, and an outer surface 67 of transfer tube 60 contacts and/or interferes with a side end portion 77 of each divider 71 to prevent specimen matter, including body fluids and solid particles, from moving or flowing between side end portion 77 and transfer tube outer surface 67 into an adjacent specimen compartment 75. Additionally, a second side end portion 79 opposing side end portion 77 preferably contacts and/or interferes with inner wall surface 25 to prevent specimen matter from moving or flowing between second side end portion 79 and inner wall surface 25 into adjacent specimen compartment 75. Thus, in one preferred embodiment of this invention, cap 40 is rotatable with respect to container 12 to align one specimen compartment 75 with field tube connection passage 52 for collection of one independent specimen, without the specimen entering and contaminating adjacent specimen compartments 75. Preferably, in order to align a desired or selected specimen compartment 75 with passage 52, a plurality of indices are formed or placed on an outer surface of container 12. Each index of the plurality of indices corresponds to one specimen compartment 75 of the plurality of specimen compartments.

Thus, the invention provides a specimen trap including a container forming a chamber. A strainer having a porous surface is positioned within the chamber, and fixedly or securely positioned within the chamber to define an upper portion of the chamber and a lower portion of the chamber. Preferably, a dividing element including a plurality of dividers, extends from a top surface of the strainer to form a plurality of specimen compartments. A plurality of supports are preferably connected to the strainer. Each support contacts a bottom surface of the container to maintain the strainer fixedly positioned within the chamber.

In one preferred embodiment of this invention, a cap is rotatably mounted with respect to the container. A first tube connection, such as a field tube connection, is mounted to the cap and forms a passage through the cap and in communication with the upper portion. A second tube, such as a transfer tube, extends through the cap and through the strainer into the lower portion. The second tube forms a passage in communication with the lower portion. Preferably, transfer tube also forms a shoulder that contacts and/or interferes with the strainer to maintain the strainer in a fixed or secured position within the chamber. The cap is rotatable with respect to the container to form communication between one of the specimen compartments and the field tube connection passage for collection of an independent specimen.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. A specimen trap comprising:
    a container forming a chamber;
    a strainer fixedly positioned within the chamber and defining an upper portion of the chamber and a lower portion of the chamber, the strainer having a porous surface providing fluidic communication between the upper portion and the lower portion;
    a dividing element extending from a top surface of the strainer, the dividing element forming a plurality of specimen compartments;
    a cap rotatably mounted with respect to the container;
    a first tube connection mounted to the cap and forming a passage through the cap and in communication with the upper portion;
    a second tube extending through the cap and extending through the strainer into the lower portion, the second tube forming a passage in communication with the lower portion, the second tube forming a shoulder interfering with the strainer to prevent the strainer from raising to a higher level within the chamber; and
    the cap rotatable with respect to the container to form communication between one of the specimen compartments and the first tube connection passage.

2. The specimen trap of claim 1 wherein a plurality of supports are connected to the strainer and maintaining the strainer in a fixed position within the chamber.

3. The specimen trap of claim 1 wherein the second tube forms a shoulder interfering with the strainer and maintaining the strainer in a fixed position within the chamber.

4. The specimen trap of claim 1 wherein the first tube connection is positioned at a periphery of the cap.

5. The specimen trap of claim 1 wherein the second tube is positioned along a rotational axis of the cap.

6. The specimen trap of claim 1 wherein the dividing element comprises a plurality of dividers, each divider extending radially outwardly from a center point of the strainer.

7. The specimen trap of claim 1 wherein the dividing element comprises a plurality of dividers, each divider extending upwardly between the top surface of the strainer and the cap.

8. The specimen trap of claim 1 wherein the dividing element is integrated with the strainer.

9. The specimen trap of claim 1 further comprising a plurality of indices on an outer surface of the container, each index of the plurality of indices corresponding to one of the specimen compartments.

10. The specimen trap of claim 1 wherein a volume of the upper portion is about equal to a volume of the lower portion.

11. The specimen trap of claim 1 wherein a volume of the upper portion is greater than a volume of the lower portion.

12. The specimen trap of claim 1 wherein the passage formed by the first tube connection provides communication between a suction field and the upper portion.

13. The specimen trap of claim 1 wherein the passage formed by the second tube provides communication between the lower portion and a suction source.

14. A specimen trap comprising:
    a container forming a chamber;
    a strainer fixedly positioned within the chamber and defining an upper portion of the chamber and a lower portion of the chamber, the strainer having a porous surface providing fluidic communication between the upper portion and the lower portion;
    a plurality of supports connected to the strainer, each support extending to a bottom surface of the container and maintaining the strainer in a fixed position within the chamber to prevent the strainer from falling to a lower level within the chamber;
    a cap mounted with respect to the container;
    a first tube connection mounted to the cap and forming a passage through the cap and in communication with the upper portion, and the second tube forming a shoulder interfering with the strainer to prevent the strainer from raising to a higher level within the chamber; and
    a second tube extending through the cap and extending through the strainer into the lower portion, the second tube forming a passage in communication with the lower portion.

15. The specimen trap of claim 14 wherein the shoulder maintains the strainer in the fixed position within the chamber.

16. The specimen trap of claim 14 wherein the cap is threadedly connected to the container.

17. The specimen trap of claim 14 wherein the cap is press-fitted on the container, and the cap rotatable with respect to the container.

18. The specimen trap of claim 14 further comprising a dividing element extending from a top surface of the strainer, and forming a plurality of specimen compartments.

19. The specimen trap of claim 18 wherein the dividing element comprises a plurality of dividers, each divider extending radially outwardly from a center point of the strainer.

20. The specimen trap of claim 18 wherein the dividing element comprises a plurality of dividers, each divider extending upwardly between the top surface of the strainer and the cap.

21. The specimen trap of claim 18 wherein the cap is rotatable with respect to the container to form communication between one of the specimen compartments and the first tube connection passage for collection of an independent specimen.

22. The specimen trap of claim 14 wherein a periphery of the strainer contacts an inner wall surface of the container.

23. The specimen trap of claim 14 wherein the passage formed by the first tube connection provides communication between a suction field and the upper portion.

24. The specimen trap of claim 14 wherein the passage formed by the second tube provides communication between the lower portion and a suction source.

25. A specimen trap comprising:
   a container forming a chamber;
   a strainer having a porous surface positioned within the chamber, the strainer fixedly positioned within the chamber and defining an upper portion of the chamber and a lower portion of the chamber;
   a dividing element extending from a top surface of the strainer, and forming a plurality of specimen compartments;
   a plurality of supports connected to the strainer, each support contacting a bottom surface of the container to prevent the strainer from falling to a lower level within the chamber;
   a cap rotatably mounted with respect to the container;
   a first tube connection mounted to the cap and forming a passage through the cap and in communication with the upper portion;
   a second tube extending through the cap and extending through the strainer into the lower portion, the second tube forming a passage in communication with the lower portion, the second tube forming a shoulder interfering with the strainer to prevent the strainer from raising to a higher level within the chamber; and
   the cap rotatable with respect to the container to form communication between one of the specimen compartments and the first tube connection passage.

26. The specimen trap of claim 25 wherein the dividing element comprises a plurality of dividers, each divider extending radially outwardly from a center point of the strainer.

27. The specimen trap of claim 25 wherein the dividing element comprises a plurality of dividers, each divider extending upwardly between the top surface of the strainer and the cap.

* * * * *